US006653122B2

(12) United States Patent
Farina et al.

(10) Patent No.: US 6,653,122 B2
(45) Date of Patent: Nov. 25, 2003

(54) INDENTIFICATION TEST DEVICE IN A RANDOM ACCESS MICROBIOLOGICAL ANALYZER

(75) Inventors: Edward Francis Farina, Oxford, PA (US); Bruce McLean Gemmell, Wilmington, DE (US); John Charles Mazza, Newark, DE (US); Michael Taylor McVey, Middletown, DE (US); Edward Stephen Kaminski, Elkton, MD (US); Antoine Elias Haddad, Newark, DE (US); Peter Louis Gebrian, Wilmington, DE (US)

(73) Assignee: Dade MicroScan Inc., Sacramento, CA (US)

( * ) Notice: Subject to any disclaimer, the term of this patent is extended or adjusted under 35 U.S.C. 154(b) by 349 days.

(21) Appl. No.: 09/841,408

(22) Filed: Apr. 24, 2001

(65) Prior Publication Data

US 2002/0155591 A1 Oct. 24, 2002

(51) Int. Cl.⁷ ................................................ C12M 1/34
(52) U.S. Cl. .................. 435/288.4; 435/287.3; 435/288.7; 422/64; 422/72
(58) Field of Search .................. 422/64, 72, 102; 435/287.1, 287.3, 288.4, 288.7

(56) References Cited

U.S. PATENT DOCUMENTS

| 3,555,284 A | 1/1971 | Anderson | 250/218 |
|---|---|---|---|
| 4,123,173 A | 10/1978 | Bulloch et al. | 356/246 |
| 4,309,384 A | * 1/1982 | Trod | 356/246 |
| 4,314,970 A | 2/1982 | Stein et al. | 422/72 |
| 4,387,164 A | 6/1983 | Hevey et al. | 436/45 |
| 4,756,883 A | 7/1988 | Romamauskas | 422/72 |
| 4,814,144 A | 3/1989 | Edelmann | 422/102 |
| 5,186,896 A | 2/1993 | Bouchee et al. | 422/72 |
| 5,256,376 A | * 10/1993 | Callan et al. | 356/246 |
| 5,266,268 A | 11/1993 | Antocci et al. | 422/72 |
| 5,409,665 A | * 4/1995 | Burd | 422/64 |
| 5,591,643 A | * 1/1997 | Schembri | 210/198.1 |
| 5,627,041 A | 5/1997 | Shartle | 435/7.24 |
| 5,631,166 A | 5/1997 | Jewell | 436/45 |
| 5,762,873 A | 6/1998 | Fanning et al. | 422/65 |
| 5,863,754 A | 1/1999 | Bajard | 435/39 |
| 6,096,272 A | 8/2000 | Clark et al. | 422/64 |
| 6,319,469 B1 | * 11/2001 | Mian et al. | 422/63 |

* cited by examiner

Primary Examiner—David A. Redding
(74) Attorney, Agent, or Firm—Leland K. Jordan

(57) ABSTRACT

A circular shaped rotor to facilitate automated identification testing of microorganisms in a microbiology analyzer having two circular arrays of microwells downwardly projecting from the top of the rotor connected to a recessed central region by a plurality of microchannels formed in the upper surface and connecting the recessed central portion to the second plurality of microwells; the rotor is further adapted to be rotated by a source of rotational energy and moved throughout the analyzer using troughs formed near its outer diameter.

14 Claims, 10 Drawing Sheets

INDENTIFICATION TEST DEVICE IN A RANDOM ACCESS MICROBIOLOGICAL ANALYZER

FIELD OF THE INVENTION

The present invention relates to an automated microbiological analyzer for determining the identity of an infecting microorganism in a liquid sample. More particularly, the present invention provides a centrifugal rotor containing the appropriate reagents for performing various microorganism identity determinations and adapted for use in a totally automated microbiological analyzer.

BACKGROUND OF THE INVENTION

Various types of clinical tests related to patient diagnosis and therapy can be performed by analysis of a biological sample. Biological samples containing the patient's microorganisms are taken from a patient's infections, bodily fluids or abscesses, plated, and placed in a suspension. The suspension is combined with appropriate reagents in analytical wells in test panels or arrays, incubated, and analyzed to aid in treatment of the patient. Automated biochemical analyzers have been developed to meet the needs of health care facilities and other institutions to accelerate analysis of patient samples and to improve the accuracy and reliability of assay results when compared to analysis using manual operations. However, with ever changing bacterial genera and newly discovered antibiotics, the demand for biochemical testing has increased in complexity and in volume. Because of these greater demands, taken in conjunction with the expense and scarcity of floor space within health care institutions and the pressure to provide clinical results at lower costs, it has become important to simultaneously perform various types of biochemical tests within a highly automated and compact analyzer that operates with minimal clinician attention using cost-effective techniques.

An important family of automated microbiological analyzers function as a diagnostic tool for determining the identity of an infecting microorganism and of an antibiotic effective in controlling growth of the infecting microorganism. In performing these test, identification and in vitro antimicrobic susceptibility patterns of microorganisms isolated from biological samples are ascertained. Such analyzers have historically placed selected biochemicals into a plurality of small sample test microwells in centrifugal rotors that contain different substrates, or in multi-well panels having antimicrobics in serial dilutions, depending on the type of test being performed. Identification (ID) of microorganisms and of Minimum Inhibitory Concentrations (MIC or AST) of an antibiotic effective against the microorganism are determined by monitoring changes in the test microwells. By examining the signal patterns generated in the array of microwells, both ID and MIC measurements and subsequent analysis may be performed by computer controlled microbiological analyzers to provide advantages in reproducibility, reduction in processing time, avoidance of transcription errors and standardization for all tests run in the laboratory.

In ID testing of a microorganism, a standardized dilution of the patient's microorganism sample, known as an inoculum, is first prepared in order to provide a bacterial or cellular suspension having a predetermined known concentration. This inoculum is placed in an analytical test array or panel having a number of microwells or alternately into a cuvette rotor assembly having a central inoculum receiving chamber from which sample is distributed by centrifugal force to a number of test microwells or chambers located at the periphery of the rotor. The test wells contain predetermined identification media typically consisting of enzyme substrates, which, depending on the species of microorganism present, will exhibit color changes, increases in turbidity or changes in fluorescence after incubation. For instance, a bacterial genera may be identified on the basis of pH changes, its ability to utilize different carbon compounds, or growth in the presence of antimicrobial agents in a test well. Some tests require addition of reagents to detect products of bacterial metabolism while others are self-indicating. In conventional chromogenic panels, the inoculum is incubated some 18–24 hours before analysis is completed. Alternately, microorganism ID may be accomplished using rapid fluorogenic test arrays employing growth-independent means in which preformed enzyme substrates are placed in the test wells and fluorogenic tests based on the detection of hydrolysis of fluorogenic substrates, pH changes following substrate utilization, production of specific metabolic substrates and the rate of production of specific metabolic byproducts are made after about 2 hours of incubation. In both cases, by examining the reaction, or lack thereof, of the inoculum and reagents after incubation and over a period of time and comparing that reaction with that of known species, the types of microorganisms can be identified. Importantly, a large number of different substrates or other reagents must be available in ID testing of an unknown microorganism because the microorganism will be more or less different sensitive to different substrates and reagents. In an automated analyzer, this is achieved by providing a variety of ID test panels, each pre-loaded with substrates and reagents that are selected to produce a known pattern of measurable reaction signals for various microorganisms.

Important challenges that must be taken into consideration when designing automated biochemical analyzers that can quickly and cost-effectively perform ID biochemical tests include the volume of reagents required per test and the cost of a ID test panel, array or other device like a centrifugal ID test rotor. Because they are small and may be produced using mass-production, plastic injection molding techniques, it is advantageous to use small sized test devices having a large number of micro-liter sized microwells for performing ID tests in order to facilitate automatic handling and minimize the expense of the ID test device. Centrifugal ID test rotors like that of the present invention typically consist of a plurality of microwells that function as reaction vessels or microwells arrayed near the periphery of a generally flat disk in which the above mentioned ID biochemical tests are conducted. An aliquot of a patient's sample is placed in each microwell along with appropriate biochemical reagents, after which the rotors is generally incubated at a controlled temperature for a period of time so that an observable reaction between the sample and reagents occurs. At predetermined time intervals, each microwell of the ID rotor is examined for an indication of changes in color change, turbidity, or other observable reaction result. The pattern of changes may then be compared with reaction signal patterns of known microorganisms enabling the identification of the any microorganism within the sample, as discussed above.

Cost-effectively providing ID test devices with the required substrates and/or reagents to perform physician requested ID tests presents technical challenges that are made increasingly difficult as the numbers of the available ID substrates and/or reagents are increased. Efforts have been made to address these challenges along with other problems and some of these employ a centrifugally activated microwell filling process using an ID rotor having a large number of micro-sized channels radially connecting the test microwells to a supply reservoir near the center of the rotor. Reagents and/or test samples are placed within the supply reservoir and moved by centrifugal force through the microchannels to the test microwells.

Typical of these rotors are those described in U.S. Pat. Nos. 4,123,173, 3,555,284 and 4,387,164. While satisfactory for their intended purposes these rotors do not fulfill all the needs that exist for a small disposable rotor that is capable of accurately providing many tests on a single sample. These rotors are comprised of two disk-like rigid plastic pieces secured together to form a closed rotor. The lower disk has a central hub for mounting on a rotor drive shaft and comprises a flat disk having a central receptacle and a plurality of peripheral cells formed therein. Each cell is separated from an adjacent cell by a raised radial ridge which forms sectors for each cell. A radial groove of capillary thickness dimensions extends from the central receptacle formed in the lower disk to the center, radially inner portion of each cell.

One problem inherent in the above designs is that different chemistries, different dilutions or different fluids are necessary; therefore, more than one central well is required. This is typically accomplished by placing a baffle in the central receptacle. Without the baffle all cells are subjected to the same pressure. With the baffle in the central cavity, due to acceleration, the cells nearest the leading edge of the baffle tend to be filled first. Also, it is sometimes difficult to fill all of the cells completely since the groove tends to become filled with liquid trying to exit the central receptacle under centrifugal force. This can result in filling differences and difficulty of completely filling a particular cell with fluid from the central receptacle.

U.S. Pat. No. 6,096,272 discloses a diagnostic microbiological testing system and method for both microorganism identification (ID) and antimicrobial susceptibility determinations (AST). The system includes multiple-well test panels capable of performing ID and AST testing on the same test panel. Each test panel is inoculated with reagents, broth-suspended organisms, and placed into the instrument system. The instrument system includes a rotating carousel for incubation and indexing, multiple light sources each emitting different wavelength light, precision calorimetric and fluorometric detection, barcode test panel tracking, and a control processor for making determinations based on measured test data.

U.S. Pat. No. 5,863,754 discloses a process for bacteria identification (ID) and for determining the sensitivity of bacteria to antibiotics (AST), and an apparatus and measuring supports for carrying out this process. A given volume of bacterial colony is introduced into a primary receiver and is dispersed within a liquid to form a precalibrated inoculum. This inoculum is moved between the primary receiver and one or more measuring supports so that the transferred quantities of bacteria correspond to the quantities required for the analyses to be carried out. Measurements are taken on the content of the compartments during or at the end of one or more incubations, and processed in order to characterize the growth of the bacteria present in the inoculum, to identify them and/or to determine their sensitivity to various antibiotics.

U.S. Pat. No. 5,631,166 discloses a disk for holding, centrifuging and microscopically viewing fluid samples. The disk includes a plurality of reaction wells radiating outwardly and includes a barrier to restrain particles during centrifugation. This disk is used in an apparatus having sample loading, mixing, centrifuging, incubating, viewing and sterilizing stations.

U.S. Pat. No. 5,627,041 discloses a rotary cartridge to present a biological sample for analysis by an imaging instrument. The cartridge utilizes a series of channels, capillaries, reservoirs and stop junctions to move a sample, reagent and diluent through the cartridge as a function of the sum of capillary, gravitational and low centrifugal forces.

U.S. Pat. No. 5,591,643 provides centrifugal rotors for delivering a biological sample to an unvented chamber in the rotor through an unmodified inlet channel. The unvented chamber is typically a cuvette comprising reagents necessary for analysis of a biological sample. The unmodified inlet channels are sized such that, as the rotor spins, gas escapes from the chamber through the inlet channel as the liquid enters the chamber through the inlet channel. The primary feature which allows the air to escape from the unvented chamber is that the cross sectional area of the inlet channel is greater than the cross sectional area of the liquid flowing through it.

U.S. Pat. No. 5,266,268 discloses a multi-well rotor which reduces tendencies of reagent or a sample material to spontaneously move or "wick" from one chamber compartment to the other, resulting in premature co-mingling of reactants, and of sample or reagent material to flow out of one or more of the outer loading ports during acceleration of the rotor for transfer of the sample or reagent material from inner chambers to corresponding outer chambers.

U.S. Pat. No. 5,186,896 discloses a cuvette rotor having at least one radially extending cuvette with a first chamber, a second chamber and a third chamber. A first barrier defines a boundary between the first and second chambers, and a second barrier defines a boundary between the second and third chambers. At least one vessel having top and bottom walls is arranged on the rotor adjacent the cuvette, the vessel being separated from the cuvette by a side wall, and the top wall of the vessel including a fourth port.

U.S. Pat. No. 4,814,144 provides a rotor unit for a centrifugal analyzer with a rotor base connected with a drive and a rotor head including chambers for the reception of a sample liquid, measuring chambers to detect components of the sample, as well as liquid channels for connecting the sample chambers with the measuring chambers. The rotor head comprises a plurality of different insert elements which are exchangeable within the rotor base at different selectable positions. Each insert element may contain pre-packed reagents in solid form which are dissolved and mixed with diluted sample.

U.S. Pat. No. 4,756,883 discloses a centrifugal analysis device in which a plastic rotor has peripheral cells each containing a reagent. The rotor is configured such that sample fluid within a central receptacle is equally dispensed to each of the peripheral cells. An outlet orifice is positioned at a radial distance greater than the inlet orifice to each cell such that each cell is completely filled with fluid, and simultaneously filled such that all reactions take place at the same beginning point.

U.S. Pat. No. 4,314,970 discloses a multicuvette rotor having a circumferential array of spaced radially extending recesses with a divider member in each recess to define a first chamber and a second chamber radially outward from the first chamber. A ring member that has a mating reference surface is seated on a reference surface of the array. A circumferential array of first optical windows is bonded to the ring member and a circumferential array of second optical windows is bonded to the base of the array in alignment with the first optical windows. A cover member has sealing surfaces that mate with edges of recesses within the array and an inner peripheral lip of the ring member to provide a continuous seal of the recesses to retain reagent and sample material to be analyzed within the recesses.

From this discussion of the art state in automated microbiological analyzers, it may be seen that microbiological analyzers employ complex multiple-well test rotors capable of performing ID testing on a sample are not truly fully automated. In particular, in the analyzer described in the family of patents related to U.S. Pat. No. 5,762,873 discussed above, prior to the start of a testing procedure, a technician manually loads a cassette with a plurality of test cards wherein the test cards come in two varieties: (1) identification cards, in which particular different growth media are placed in each of the wells of the card when the cards are manufactured, and (2) susceptibility cards, in which different concentrations of different antibiotics are placed in each of the wells of the card. In the analyzer described in U.S. Pat. No. 6,096,272 discussed above, a technician must inoculate a combination ID/AST test panel with an unknown microorganism and then manually place that panel into the analyzer where it is then incubated and analyzed periodically. From this it may be seen that prior to the use of such state-of-the art microbiological analyzers, an operator is required to select the particular ID and/or AST test cards or devices that are required to perform the analyses called for by a physician and then either: (1) to inoculate and load the selected ID and/or AST test cards onto the analyzer, or (2) to load the selected ID and/or AST test cards onto the analyzer where the cards are automatically inoculated with test sample.

In addition, ID test rotors are frequently provided with a number of complexly configured microchannels, cover members that must seal with base members, various outlet and inlet orifices, channels, capillaries, reservoirs and stop junctions, etc., to uniformly transfer a given amount of sample from a loading port to a number of ID test microwells. These features are costly to provide.

Hence there remains a unmet need for improved ID test rotors pre-loaded with the substrates, growth media and/or reagents required to perform a wide variety of ID determinations adapted for use in a fully automated microbiological analyzer having the flexibility to perform a wide variety of ID determinations without requiring a technician to pre-select and individually load rotors onto the analyzer. There is an even further need for such an ID rotor to have low-cost manufacturing features and to be simply operable via centrifugal means to uniformly distribute a sample to a large number of small ID test microwells.

SUMMARY OF THE INVENTION

The present invention meets the foregoing needs by providing a simple and low-cost ID test rotor adapted for performing different ID tests and for use in a fully automated microbiological test analyzer. A particular embodiment of the present invention is directed at an ID test rotor preloaded with substrates and reagents that are selected to produce a known pattern of measurable reaction signals that correspond to the identity of various known microorganisms. Incoming patient samples to be tested are bar-coated with identifying indicia from which the ID tests that are desired to be accomplished may be established by the analyzer. The analyzer then automatically selects the numbers of different ID test rotors required to complete the requested ID protocols from rotors housed in a number of different tube-like ID canisters maintained on a rotatable carousel. The ID test rotors have unique features that enable a rotor to be removed from the canister, to be easily loaded with sample, to be subjected to a centrifuging action, to be transported to a sample incubation and testing station, and to be positioned within such an incubation and testing station where the ID rotor may be examined for reaction results. Test results obtained from a plurality of microwells located in a pair of circular arrays are automatically compared with reaction signal patterns of known microorganisms thereby enabling the identification of any microorganism within the sample.

BRIEF DESCRIPTION OF THE DRAWINGS

These and other features and advantages of the present invention can best be understood by reference to the detailed description of the preferred embodiments set forth below taken with the drawings in which.

DETAILED DESCRIPTION OF THE PREFERRED EMBODIMENTS

Figure 1:
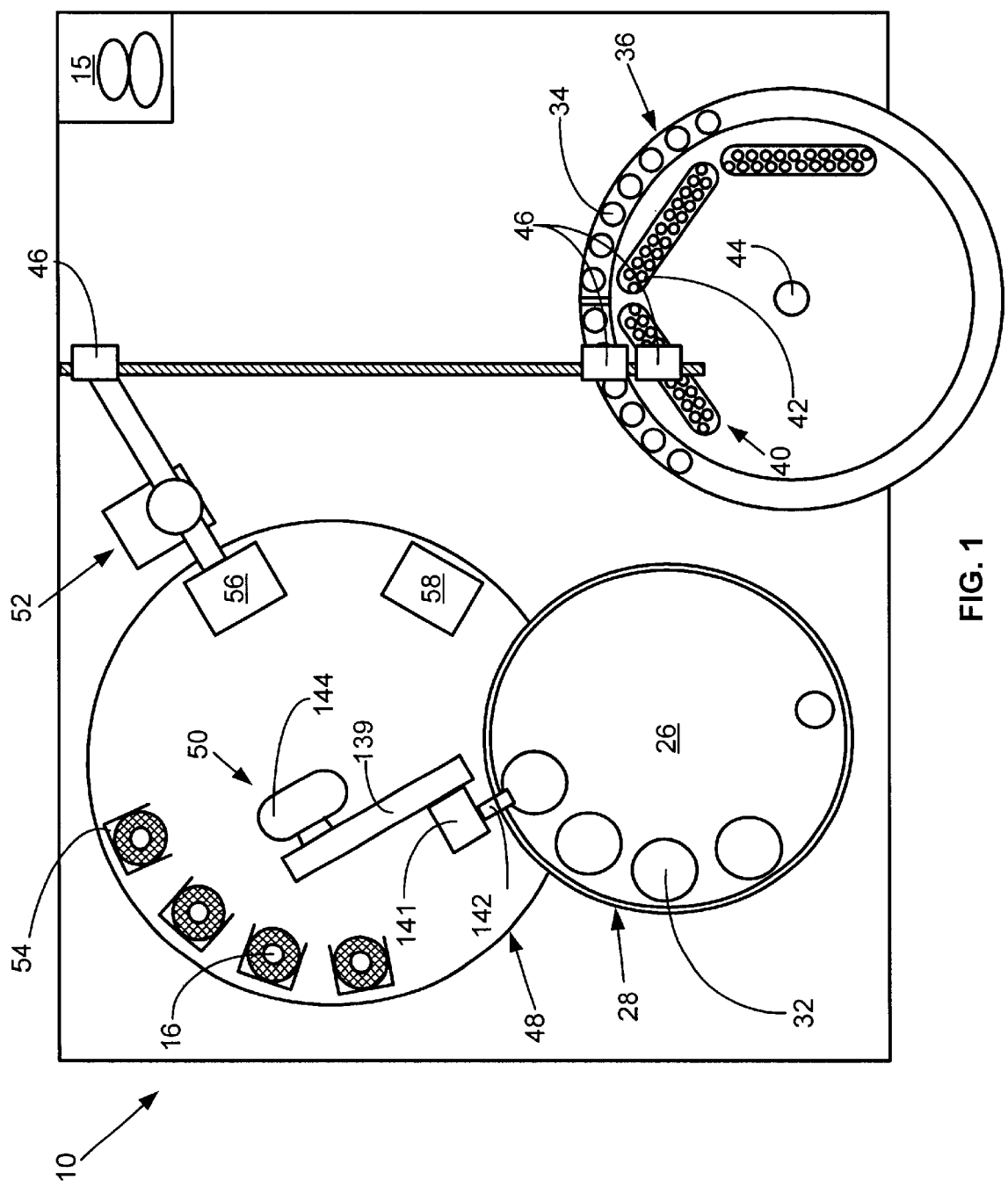
FIG. 1 is a simplified schematic top plan view of an automated microbiological analyzer in which the ID test rotor of the present invention may be used.
Figure 2:
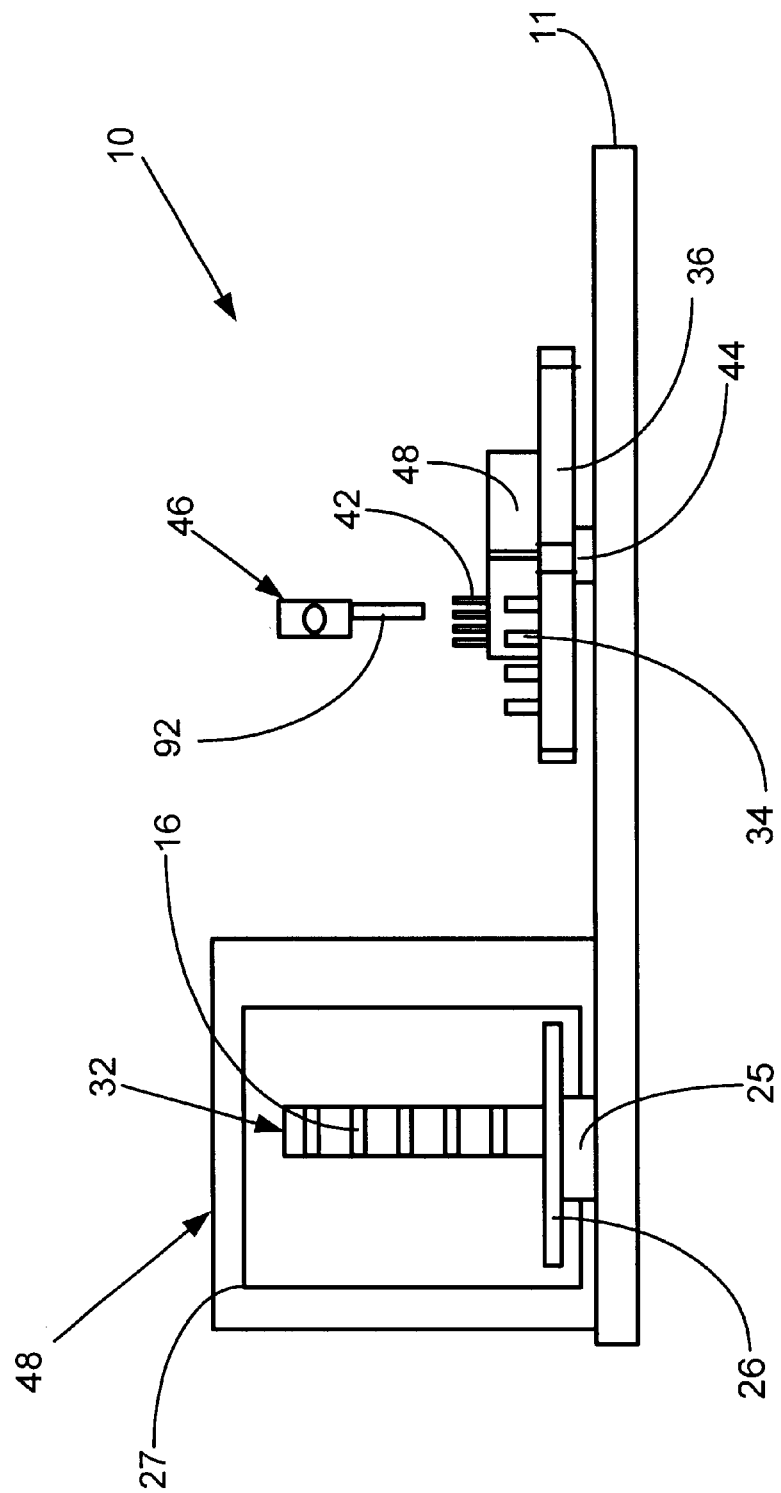
FIG. 2 is a simplified schematic elevation view of the automated microbiological analyzer of FIG. 1.

FIG. 1 schematically illustrates a random access automated microbiological analyzer 10 in which the present invention may be used to advantage. Analyzer 10 has a plurality of different ID test rotors 16 that are maintained in an inventory on-board or within analyzer 10 in different tube-like ID canisters 32. ID canisters 32 are mounted on a rotatable carousel 26, hereinafter called the ID carousel 26 that is housed within an environmentally controlled ID chamber 28. The different ID test rotors 16 are preloaded with different substrates and reagents that have been selected to produce different patterns of measurable reaction signals which patterns may be compared with reaction signal patterns that are known to correspond to different known microorganisms. The ID of an unknown microorganism in a sample may then be determined by analyzing the test results of the sample using one or more different ID rotors 16. The ID carousel 26 may be rotated by a carousel motor 25 (FIG. 2) so as to present any one of the ID canisters 32 to a robotic device 50 within an ID incubation and testing chamber 48 described hereinafter. In a preferred embodiment, as many as eighty ID test rotors 16 are contained within each ID canister 32 and as many as five ID canisters 32 are housed within the ID carousel 26. Analyzer 10 is equipped with an on-board CPU computer 15 programmed using well-known techniques to automatically operate all features of analyzer 10 described hereinafter, including a sample barcode scanner to ascertain the identity of a sample and of the ID tests to be performed.

Figure 3:
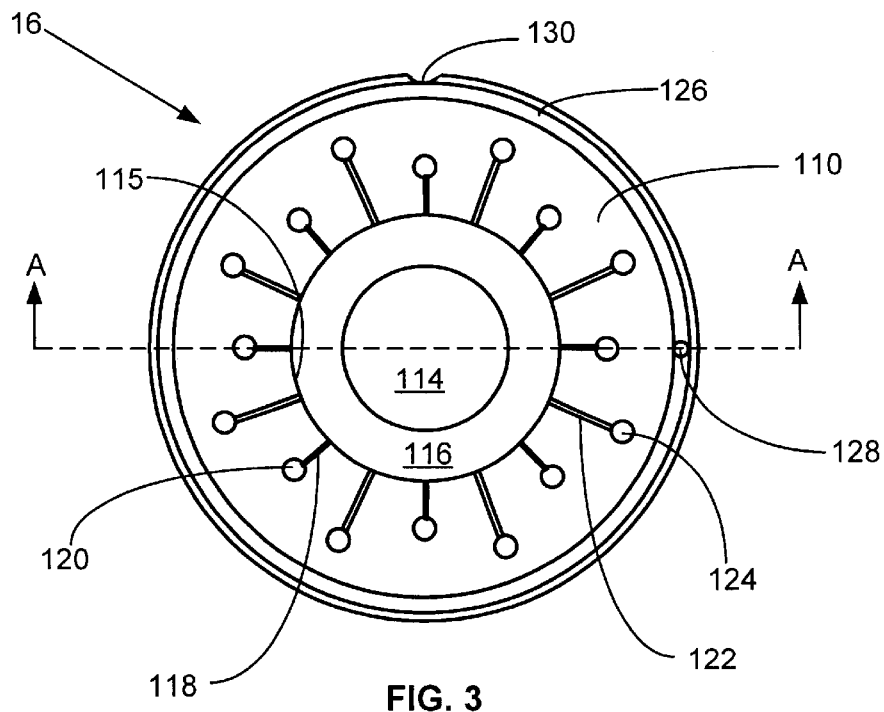
FIG. 3 is a top plan view of an ID rotor in accordance with the present invention and useful within the analyzer of FIG. 1.
Figure 5:
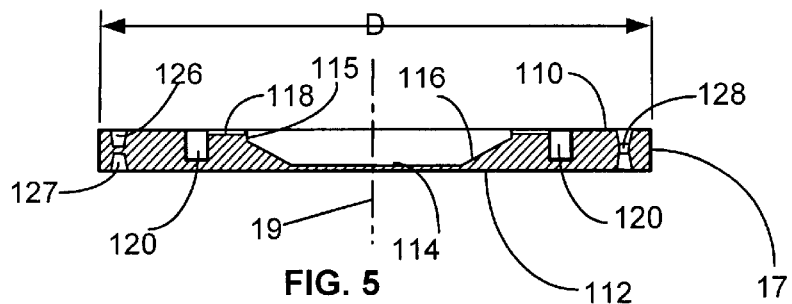
FIG. 5 is a cross-section view of the ID rotor of FIG. 3.

FIG. 3 is a top plan view of the ID test rotor 16 of the present invention, the rotor 16 comprising a top surface 110 and a bottom surface 112 seen in FIG. 5. ID test rotor 16 has a central axis 19, a diameter D, and a generally vertical radial sidewall 17 connecting the top surface 110 and bottom surface 112 at the diameter D of the rotor 16. A closed central portion 114 is recessed below the top surface 110 of rotor 16. A first plurality of downwardly projecting microwells 120 is formed in the upper surface and distributed equidistant from one another in a first circular array located at a first distance from the central axis 19; a second plurality of downwardly projecting microwells 124 is formed in the upper surface 110 and distributed equidistant from one another in a second circular array, located at a second distance from the central axis, the second distance being larger than the first distance; a first plurality of downwardly projecting microchannels 118 is formed in the upper surface and connecting the recessed central portion 114 to the first plurality of microwells 120; a second plurality of downwardly projecting microchannels 122 is formed in the upper surface 110 and connecting the recessed central portion 114 to the second plurality of microwells 124. For purposes of simplicity in illustration, FIG. 3 shows only a limited number of microwells 120 and 124, microchannels 118 and 122, and is not intended to be restrictive.

The recessed circular centermost portion 114 is surrounded by a generally inclined annulus portion 116. The plurality of first microchannels 118 extends radially outwards from a radial wall 115 formed vertically at the outer periphery of annulus portion 116 to the first circular array of equally spaced microwells 120; the plurality of second equally spaced microchannels 122 also extends radially outwards from the radial wall 115 to the second circular array of microwells 124. The length of microchannels 118 is generally about ½ to ⅔ the radial length of microchannels 122. The two arrays of equally spaced microwells 120 and 124 are a key feature of rotor 16 since the two arrays allow for a much greater number of test wells 120 and 124 that is typically possible with conventional centrifugal rotors having a single array of test wells equidistant from the center of the rotor. The first and second plurality of downwardly projecting microwells 120 and 124 are shaped and sized equally and the first and second plurality of microchannels 118 and 122 have the same cross-section depth and width dimensions.

FIG. 5 shows an additional key feature of rotor 16 as a top radial trough 126 formed in the top surface and a bottom radial trough 127 formed in the bottom surface, the top 126 and bottom 127 troughs are vertically aligned with one another but do not intersect one another and are provided to facilitate handling of the rotor 16 by ID robotic device 50 and by an ID rotor filling and centrifuging apparatus 52 described hereinafter. Another feature of rotor 16 is a through opening 128 formed between the top radial trough 126 and the bottom radial trough 127 thus fully extending from the top surface 110 to the bottom surface 112 to facilitate radial positioning of rotor 116 within an ID analysis station 56 described hereinafter. Optionally, a small notch 130 may be formed in sidewall 17 and made to fully extend from the top surface 110 to the bottom surface 112 to facilitate reagent pre-loading of microwells 120 and 124 during a manufacturing process.

In an exemplary embodiment, rotor 16 comprises a body of polystyrene like Dow Chemical 666D or similar moldable polymeric material and is about 0.150 inches thick and about 2 to 2.5 inches in diameter; microwells 120 and 124 are similar to one another in size and dimensions and have a diameter at the closed end in the range of about 0.090 to 0.094 inches; the walls of the microwells 120 and 124 are inclined slightly outwards to aid in removal during a molding process so that the diameter at the open end is in the range of about 0.100 to 0.108 inches. The depth of microwells 120 and 124 is in the range of about 0.090 to 0.110 inches and microchannels 118 and 122 are similar in cross-section dimensions and have a width in the range of about 0.014 to 0.016 inches and a depth in the range of about 0.014 to 0.016 inches.

Figure 5A:
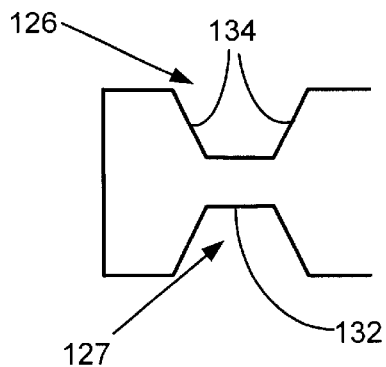
FIG. 5A is an enlarged view of a handling feature of the ID rotor of FIG. 3.
Figure 4:
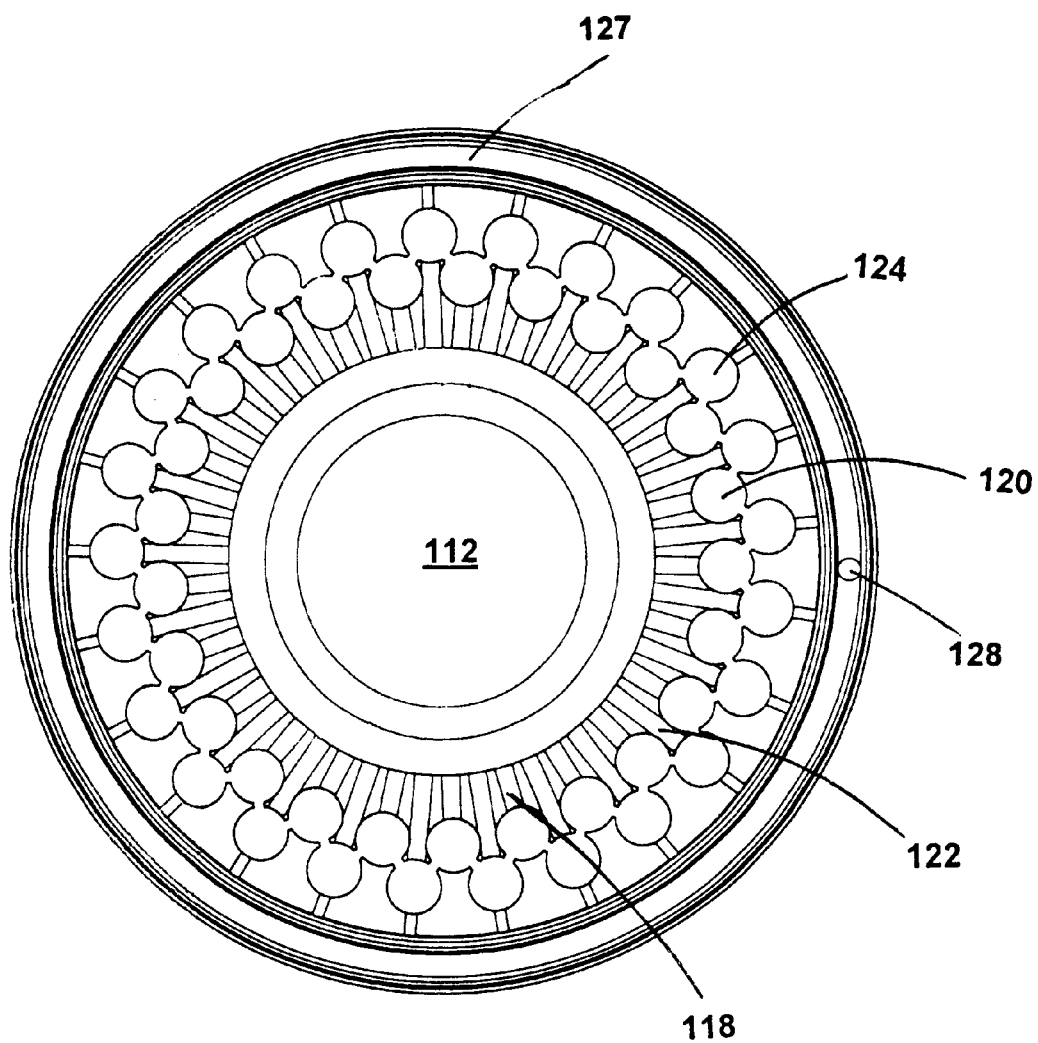
FIG. 4 is a bottom plan view of an ID rotor in accordance with the present invention and useful within the analyzer of FIG. 1.

FIG. 5 is a cross-sectional view of rotor 16 along line A—A in FIG. 3 showing the relative positioning of top surface 110 bottom surface 112, the recessed circular centermost portion 114 and inclined annulus portion 116. FIG. 5 shows only first microchannels 118 and microwells 120; in FIG. 5A, troughs 126 and 127 are seen as equally formed in both surfaces 110 and 112 and have flat bottoms 132 and trough walls 134 inclined at about 30-degrees thereto. In the embodiment mentioned above, the flat bottom 132 is about 0.060 inches wide between the trough walls 134 and the trough walls 134 are about 0.060 inches high.

Figure 6:
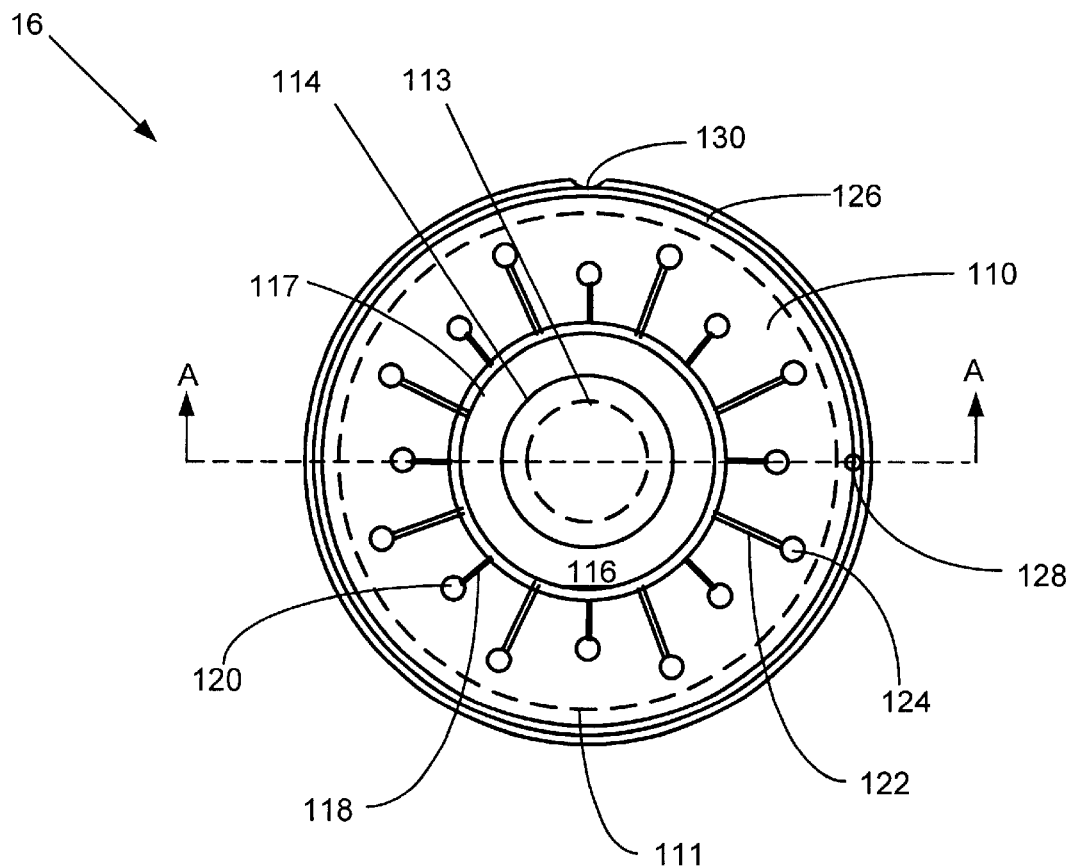
FIG. 6 is a top plan view of an alternate ID rotor in accord with the present invention and useful within the analyzer of FIG. 1.

FIG. 6 illustrates an alternate embodiment of the ID test rotor 16 of the present invention in which a circular, thin layer 111 of tape stock is shown in dashed lines for clarity and has an opening 113, also shown in dashed lines, formed at its center and adhesively adhered to the top surface 110 of the rotor 16. Tape stock layer 111 is positioned so that the opening 113 in the tape stock layer 111 is aligned over the recessed central portion of the rotor. Opening 113 is provided within the tape stock layer 111 to allow free access by a sample dispensing mechanism to a sample receiving chamber formed by surfaces 114, 116 and 115 and tape stock layer 111. The opening 113 in tape stock layer 111 is generally aligned with the recessed circular centermost portion 114 but has a smaller diameter than that of the centermost portion 114. Tape stock layer 111 is typically made of a thin layer of about 2 to 4 mils thickness of a plastic material like polypropylene or polyester or the like and is affixed to the top surface 110 with adhesive.

Figure 6A:
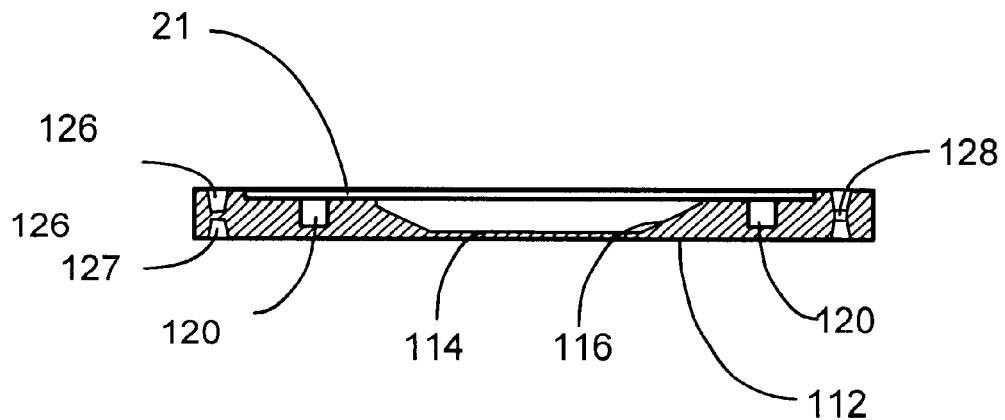
FIG. 6A is a cross-section view of the ID rotor of FIG. 6.

FIG. 6A illustrates another alternate embodiment of the ID test rotor 16 of the present invention of FIG. 5 in which a thin flat recess 21, not shown to size, is formed in the top surface 110 with dimensions to accept tape stock layer 111 within recess 21. Preferably, recess 21 has a depth of about 0.005 to 0.015 inches in depth so that the top of tape stock layer 111 may be aligned below the top surface 110 of rotor 16. For purposes of clarity, tape stock layer 111 is not shown placed within recess 21. In such an embodiment, a number of ID rotors 16 may be stacked atop one another with the top surface 110 of one rotor 16 in contact with the bottom surface 112 of an adjacent rotor 16. Recess 21 thereby prevents contact between the tape stock layer 111 and the bottom surface 112 of the adjacent rotor 16. FIG. 6A illustrates the ID test rotor 16 of the present invention in which tape stock layer 111 is placed into the recess 21.

Figure 6B:
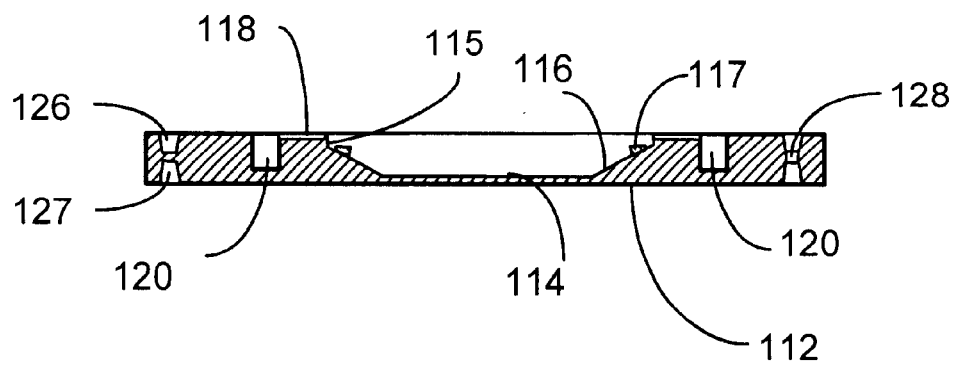
FIG. 6B is a cross-section view of an alternate version of the ID rotor of FIG. 6.
Figure 8:
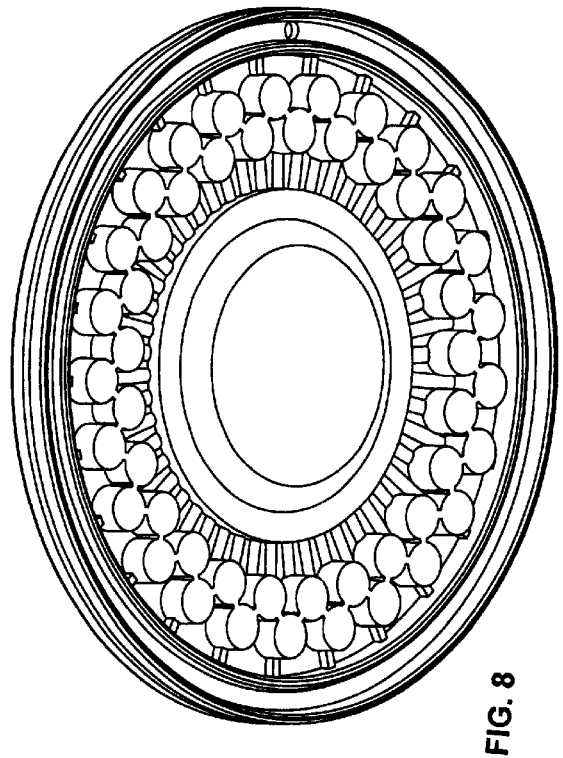
FIG. 8 is a perspective view of the bottom of an ID rotor in accord with the present invention.
Figure 7:
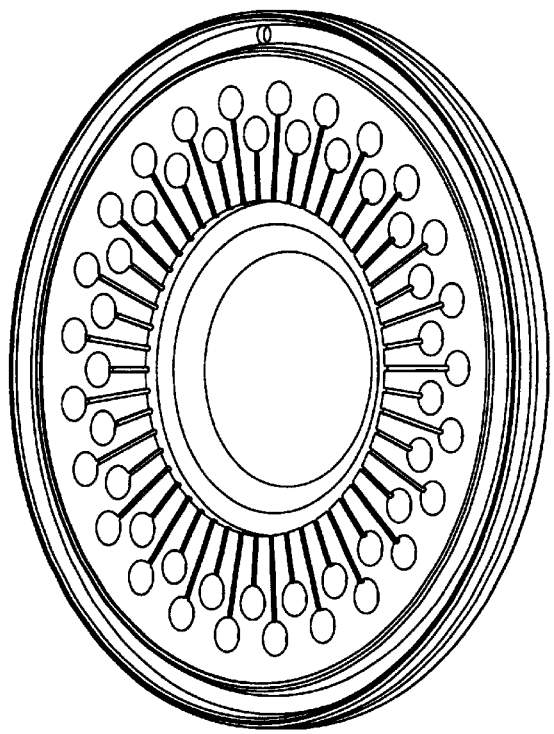
FIG. 7 is a perspective view of the top of an ID rotor in accord with the present invention.

FIG. 6B illustrates another alternate embodiment of the ID test rotor 16 of the present invention in which the radial annular portion 116 further comprises a radial ridge 117 positioned proximate the first and second plurality of microchannels 118 and 122 and projects upwards from the surface of the annular portion 116. Ridge 117 acts somewhat like a barrier in retaining a portion of sample fluids that are forced through microchannels 118 and 122 into microwells 120 and 124 in a filling process described hereinafter. In use, the retained sample portion is sacrificially evaporated and thereby acts to eliminate evaporation of sample within microchannels 118 and 120 and microwells 122 and 124. FIG. 7 is a perspective view of the top of an ID rotor 16 in accord with the present invention and FIG. 8 is a perspective view of the bottom of an ID rotor 16 in accord with the present invention.

Analyzer 10 comprises two separate incubation and analysis chambers as required for ID and AST testing. An ID incubation and analysis chamber 48 is seen in the top plan schematic view of FIG. 1 with its uppermost surface removed to expose an interior portion in which an ID robotic device 50, also seen in FIG. 10, is adapted to remove different ID test rotors 16 from ID canisters 32 and to then move the ID test rotors 16 to and from a filling and centrifuging apparatus 52 moveable between the ID incubation chamber 48 and a sample pipetting and transport system 82 described hereinafter and illustrated in FIG. 9. ID robotic device 50 comprises a robotic arm 142 controlled by a retractable gear-and-pinion mechanism 141 and has a pair of claw-like gripping pincer-notches 145 at one end of arm 142 sized and spaced to grip trough 126 in rotor 16 thereby to move the lowermost ID rotor 16 from ID canister 32 to centrifuging apparatus 52 when centrifuging apparatus 52 is positioned within the ID incubation and analysis chamber 48. A vertically translatable motor 144 provides angular motion to a swing arm 139 within robotic device 50 so that ID rotors 16 may positioned throughout all of the incubation and analysis chamber 48. Devices that perform the functions of robotic device 50 are well known in the art as computer-controlled pick-and-place robotic devices.

The robotic device 50 (FIG. 10) comprises a CPU computer 15 controlled motor-driven apparatus adapted for movement in x-y, in-out and vertical directions so as to be able to move ID rotors 16 within analyzer 10 as previously described. Device 50 may take on many alternate designs but typically includes rack and pinion gears 141 and/or rotating drive and toothed socket mechanisms 143. An important feature of device 50 is a pair of teeth 145 that are located at the end of a robotic arm 142 and controlled with a spring-activated normally-closed incisor motion. Teeth 145 are sized to fit into troughs 126 and 127 thereby to secure ID rotor 16 for movement as required within analyzer 10. In the event of a power failure, any ID rotor 16 held within teeth 145 on robotic arm 142 is retained securely because of normally-closed, spring-activation clamping action of device 50. Flexible and secure transportation of an ID rotor 16 between the automated features of analyzer 10 is made possible by the presence of troughs 126 and 127 as the ID rotor 16 is constrained by any number of differently designed robotic devices 50.

ID robotic device 50 is further adapted to remove ID test rotors 16 from the filling and centrifuging apparatus 52 (when centrifuging apparatus 52 is positioned within the ID incubation chamber 48) to either a rotor holding frame 54 or an ID analysis station 56 both of which are located within the ID incubation and analysis chamber 48. ID robotic device 50 is additionally adapted to move ID test rotors 16 between a rotor holding frame 54 and to a disposal station 58 within the ID incubation chamber 48. In an exemplary embodiment, as many as three rotor holding frames 54 may be attached to the interior walls of the ID incubation chamber 48 and as many as twenty-seven ID test rotors 16 may be mounted within each rotor holding frame 54. Typically, rotor holding frames 54 are horizontally oriented C-clamp shaped pieces of spring metal in which the ears of the holding frames 54 are adjusted to provide an small, sliding interference fit between the holding frames 54 and an ID rotor 16 so as to secure ID test rotors 16 within each rotor holding frame 54.

Figure 11:
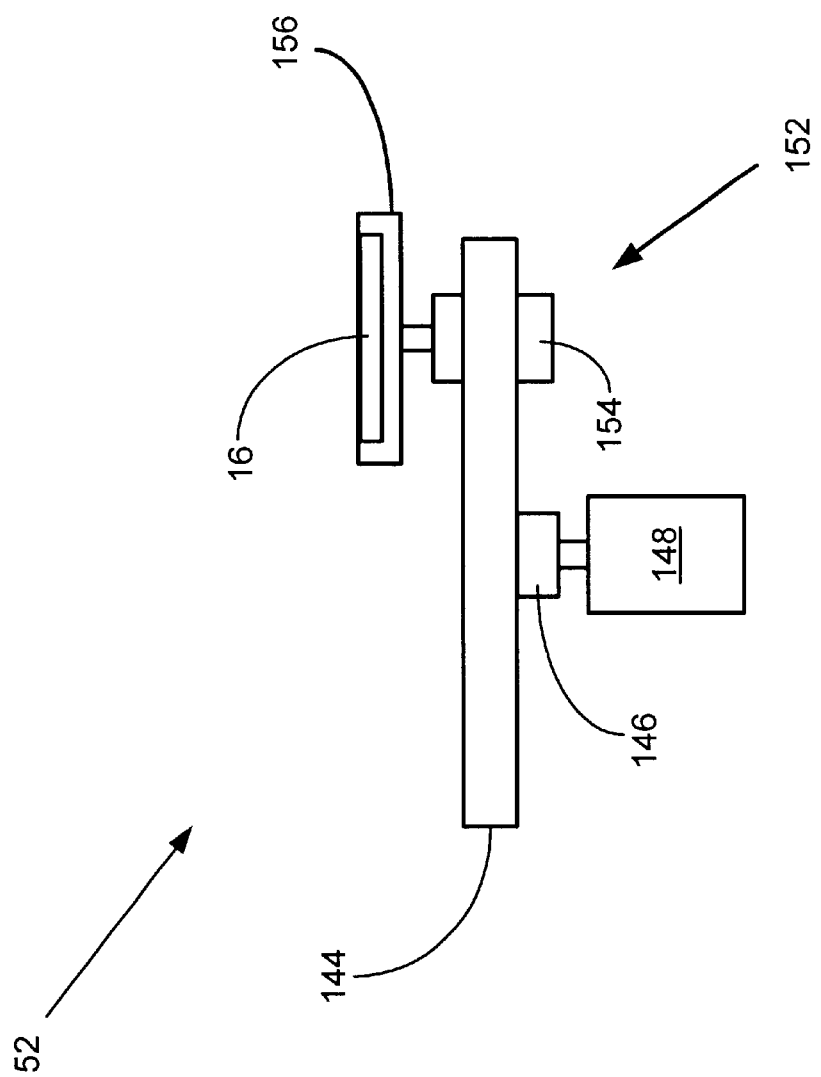

The ID rotor filling and centrifuging apparatus 52 (FIG. 11) comprises a moveable arm 144 mounted to a rotatable support 146 rotated by a motor 148 so that arm 144 may be swung in a plane between ID incubation and testing chamber 48 and a rotor loading position 46e described hereinafter located proximate a sample pipetting and transport system 82 as described hereinafter. An important feature of the filling and centrifuging apparatus 52 is a centrifuging module 152 adapted to provide rotational motion to an ID rotor 16 mounted within a ID rotor clamping mechanism 156, the centrifuging module 152 being mounted on moveable arm 144. Centrifuging module 152 typically comprises a motor 154 capable of rotating ID rotor 16 at an initial relatively low speed in the range of about 200 to 400 RPM and also at a relatively high speed in the range of about 4,000 to 6,000 RPM. ID rotor clamping mechanism 156 is adapted to securely grasp ID rotor 16 at its periphery. As described later, liquid sample is initially loaded into rotor 16 in a low RPM operation and then moved to microwells 120 and 124 in a higher RPM operation. Motors that enable the rotational functions of centrifuging module 152 are known in the art as variable speed motors and are commercially available from a number of sources.

The ID analysis station 56 comprises a fluorometric reader similar to that used in the MicroScan "Walk-Away" microbiology analyzer sold by Dade Behring Inc., Deerfield, Ill. U.S. Pat. Nos. 4,676,951, 4,643,879, 4,681,741 and 5,645,800 describe certain features of the Walk-Away system. The ID analysis station 56 includes a pair of stationary reading heads that reside above the two annular arrays of test microwells 120 and 124 in ID rotor 16 when rotor 16 is placed within analysis station 56. Each reading head encloses a fluorometer having a source lamp that directs light to an excitation filter through a quartz light path. A pair of lenses or dichromatic beam splitters direct the out coming light onto sample contained either in a single underlying microwells 120 or 124 within ID rotor 16. The microwell is preloaded with a material that, in the presence of a target microorganism within sample fluids displaced into the microwells as described hereinafter, reacts to the light energy by fluorescing. The resulting fluorescence is directed by lenses or mirrors to an emission filter for the expected wavelength. Solid state detectors capture the fluoresced light signal from each of wells 120 or 124 as the ID rotor is rotated below the reading heads and translate the light signal into an output that is proportional to the amount of fluorescence detected. Measured signals are transmitted to the on-board CPU computer 15 so that the pattern of signals emanating from the microwells 120 and 124 may be compared with signal patterns of known microorganisms. The identity ID of any microorganisms within the sample may thereby be determined.

Analyzer 10 also has AST test and broth containers (not shown) adapted for performing different AST tests as requested by a physician.

Patient samples are presented to the analyzer 10 in open sample tubes 34 placed in openings in a number of sample tube holders 36 located near the periphery of a rotatable circular tray 38, rotatable by a tray motor 44. Sample tube holders 36 are generally curved, each forming a portion of the circumference of a circle. Two of such sample tube holders 36 are seen in FIG. 1 supported on rotatable circular tray 38, however any number of sample tube holders 36 may be sized and adapted to fit onto the circular tray 38. The circular tray 38 also supports a number of pipette tip holders 40 located in the innermost portion of circular tray 38. Pipette tip holders 40 are generally elongate in shape and each pipette tip holder 40 is adapted to hold a plurality of disposable pipette tips 42. Six of such pipette tip holders 40 are seen in FIG. 1, however any number of pipette tip holders 40 may be sized and adapted to fit onto the circular tray 38. The rotatable circular tray 38 is hereinafter called the S/PT tray 38. The S/PT tray 38 may be rotated by motor 44 so as to present any of the pipette tips 42 and any of the open sample tubes 34 to a pipetting apparatus 46. The pipetting apparatus 46 is adapted to remove one of the pipette tips 42 from pipette tip holder 40 and to next insert the pipette tip 42 into an open sample tube 34 and extract a known amount of patient sample from the sample tube 34 into the pipette tip 42.

The circular tray 38, pipetting apparatus 46, ID carousel 26, and ID incubation chamber 48 are all supported above an upper operating plate 11 that provides an operating structure for analyzer 10. A lower base plate 13, typically mounted on rollers, provides a base for additional operating structures within analyzer 10.

Figure 9:
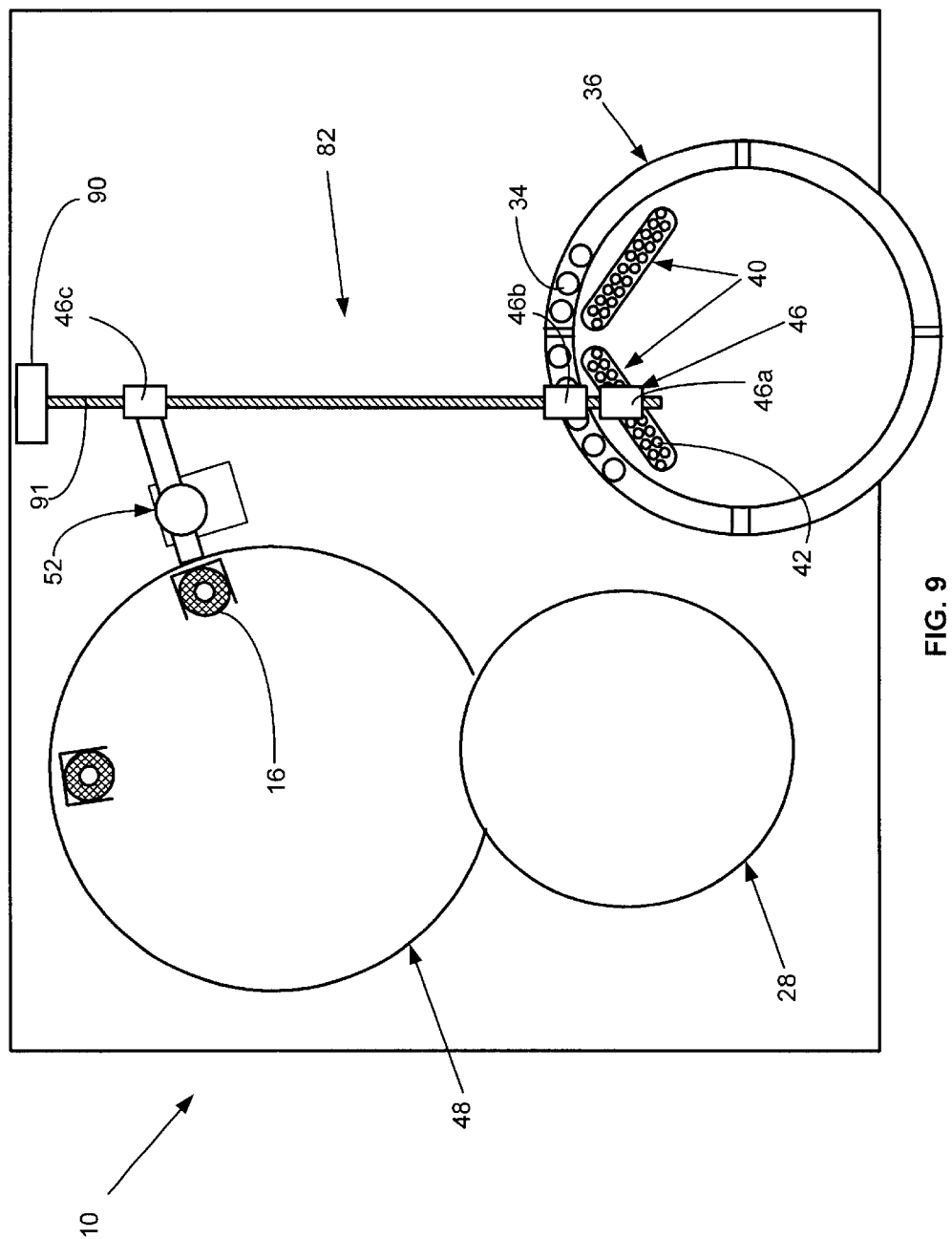
FIG. 9 is a simplified schematic plan view of a transport system in relation to portions of the analyzer of FIG. 1.
Figure 10:
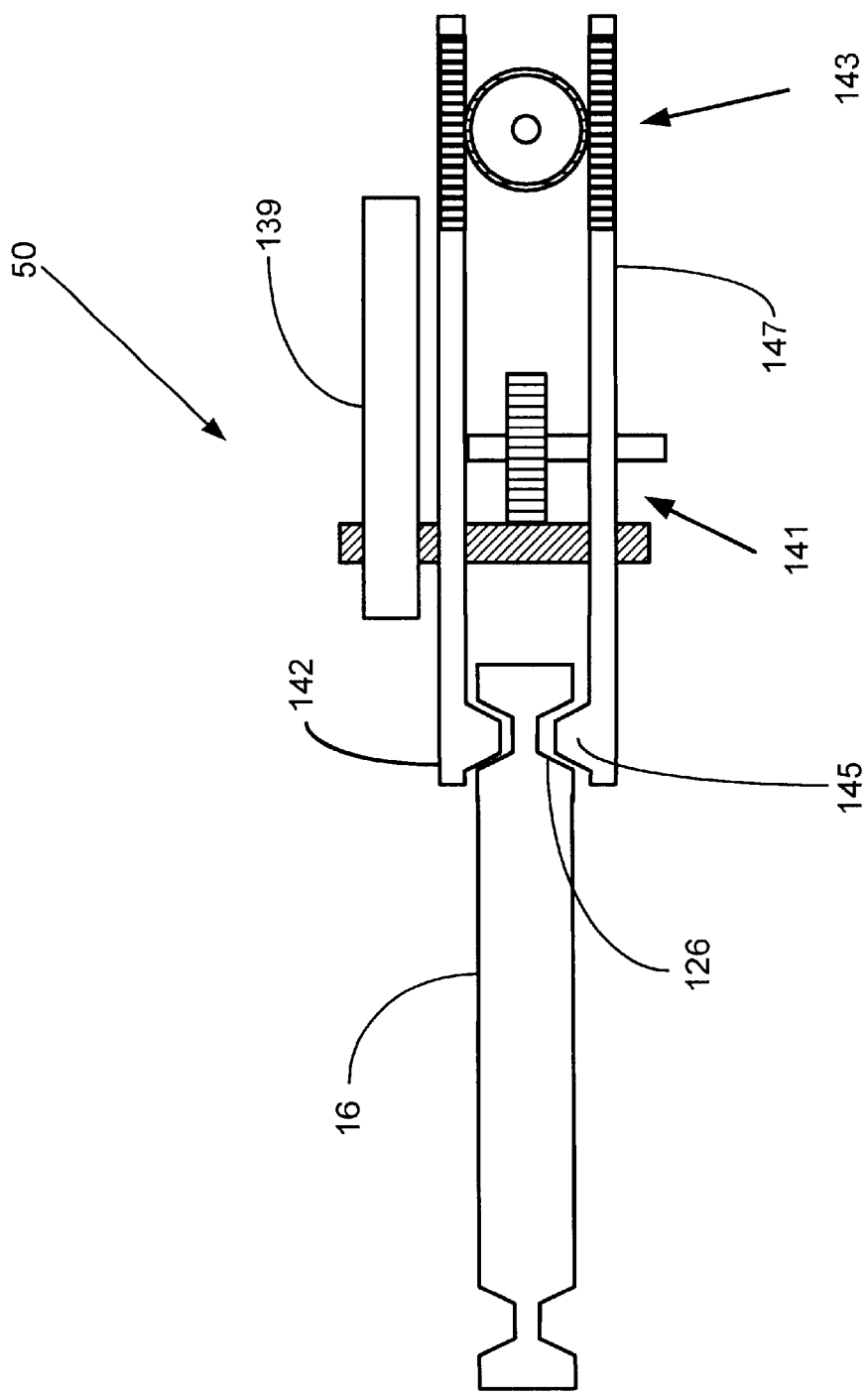
FIG. 10 is a simplified elevation view of a robotic handling apparatus useful for transporting an ID rotor in accordance with the present invention and within the analyzer of FIG. 1; and, FIG. 11 is a simplified schematic elevation view of a centrifugal handling apparatus useful for transporting an ID rotor in accordance with the present invention and within the analyzer of FIG. 1.

An important feature of the analyzer 10 is a multi-functional liquid sample pipetting and transport system 82 illustrated schematically in FIG. 9 in which only some of the features and elements of analyzer 10 are depicted for the sake of simplicity. The sample pipetting and transport system 82 is adapted to remove a pipette tip 42 from a pipette tip holder 40 using pipetting apparatus 46, aspirate a liquid sample from an open sample tube 34 held in a sample tube holder 36 and then deposit a portion or all of the aspirated sample into an ID test rotor 16. The pipetting apparatus 46 is supported on a raised frame (not shown) and is adapted to be moved by a motor 90 and thread-rod 91 randomly between a first position, identified as 46a, for accessing tips 42, a second position, identified as 46b, for aspirating sample from tube 34, a third position, identified as 46c, for depositing a known amount of sample into an ID test rotor 16.

As previously described, the ID rotor filling and centrifuging apparatus 52 is adapted to remove an ID test rotor 16 from the ID incubation and analysis chamber 48 and present the ID test rotor 16 to the pipetting apparatus 46. The ID rotor filling and centrifuging apparatus 52 is further adapted to replace an ID test rotor 16 back into the ID incubation chamber 48 after presentation to the pipetting apparatus 46. The ID rotor filling and centrifuging apparatus 52 is even further adapted to centrifugally rotate an ID test rotor 16 so as to distribute sample deposited therein by the pipetting apparatus 46.

In operation of analyzer 10, incoming patient samples to be tested have been bar-coated with identifying indicia from which the ID and AST tests that are desired to be accomplished may be established using well-known computer-based programming protocols. Computer CPU 15 is programmed to automatically determine a particular ID canister 32 having the appropriate ID test rotors 16 required to complete the requested ID protocol(s) and presents the appropriate ID canister 32 to the robotic device 50. Robotic device 50 removes a ID test rotor 16 from the selected ID canister 32 and then moves the selected ID test rotor 16 into ID incubation chamber 48 and loads the rotor 16 onto the filling and centrifuging apparatus 52. At the same time, sample pipetting and transport system 82 and pipetting apparatus 46 are controlled by CPU 15 to make available at position 46e the required amount of sample fluid for which the ID protocol to be performed has been requested. Filling and centrifuging apparatus 52 next moves ID test rotor 16 into position 46e where of sample fluid for the ID protocol is deposited into rotor 16 through opening 113 in tape 111.

As rotor 16 is initially loaded with liquid sample, centrifuging module 152 portion of filling and centrifuging apparatus 52 is activated to rotate ID rotor 16 at an initial relatively low speed in the range of about 200 to 400 RPM for a period of time in the range 1–3 seconds during which surface tension of the sample is overcome by centrifugal forces and sample is moved away from the centermost portion of surface 114 and upwards along surface 116. The centrifuging module 152 is next activated to rotate ID rotor 16 for a period of time in the range 5–15 seconds at a speed in the range of about 4,000 to 6,000 RPM during which sample is moved through microchannels 118 and 122 into microwells 120 and 124 respectively. Subsequent to this loading and filling operation, rotation of ID rotor 16 is stopped, and ridge 117 serves to act as a barrier so that a retained sample portion is sacrificially evaporated thereby eliminating evaporation of sample within microchannels 118 and 122 and microwells 120 and 124.

Loaded ID rotors 16 are next moved back into ID incubation and test chamber where rotors 16 are removed from the filling and centrifuging apparatus 52 and, optionally, may be moved by robotic means 50 to analyzer 56 where an initial read may be made of fluorescence signals emanating from loaded microwells 120 and 124. Robotic means 50 then places ID rotors 16 into incubation frames 54 for various periods of time, depending on the particular ID test protocol being performed by analyzer 10 under control of CPU 15. As is known, during incubation, fluorescence signals emanating from loaded microwells 120 and 124 are measured at predetermined time intervals using robotic means 50 to move ID rotors to and from racks 54 as required to and from analyzer 56. After the completion of a ID test protocol, ID rotors 16 are deposited in trash receptacle 58.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. A test device adapted to facilitate automated identification testing of microorganisms in a microbiology analyzer, the test device comprising:

a circular rotor with opposed top and bottom surfaces, said rotor having a central axis, a diameter, a generally vertical radial sidewall connecting the top and bottom surfaces at the diameter of the rotor, and having a central portion recessed below the top surface;

a first plurality of downwardly projecting microwells formed in the upper surface and distributed equidistant from one another in a first circular array located at a first distance from the central axis;

a second plurality of downwardly projecting microwells formed in the upper surface and distributed equidistant from one another in a second circular array, located at a second distance from the central axis, the second distance being smaller than the first distance;

a first plurality of downwardly projecting microchannels formed in the upper surface and connecting the recessed central portion to the first plurality of microwells;

a second plurality of downwardly projecting microchannels formed in the upper surface and connecting the recessed central portion to the second plurality of microwells;

wherein the rotor is adapted to be rotated by a source of rotational energy.

2. The rotor of claim 1 further comprising a circular, thin layer of tape stock having an opening formed at its center and adhered to the top surface of the rotor and positioned in the recess so that the opening in the tape stock is aligned over the recessed central portion of the rotor.

3. The rotor of claim 1 further comprising a top radial trough formed in the top surface and a bottom radial trough formed in the bottom surface, the top and bottom troughs vertically aligned with one another but do not intersect one another.

4. The rotor of claim 3 further comprising a through opening formed between the top radial trough and the bottom radial trough.

5. The rotor of claim 1 wherein the recessed central portion comprises a generally flat center portion and a connected radial annular portion inclined upwards from the flat center, the first and second plurality of microchannels connecting to the radial annular portion.

6. The rotor of claim 5 wherein the radial annular portion further comprises a radial ridge positioned proximate the first and second plurality of microchannels and projecting upwards from the surface of the annular portion.

7. The rotor of claim 1 wherein the first and second plurality of downwardly projecting microwells are shaped and sized equally.

8. The rotor of claim 1 wherein the first and second plurality of microchannels have the same cross-section depth and width dimensions.

9. The rotor of claim 1 wherein the radial sidewall is about 0.150 inches height and the diameter of the rotor is about 2.4 inches distance.

10. The rotor of claim 1 wherein the microwells are similar in size and dimensions and have a diameter at a closed end in the range of about 0.090 to 0.094 inches, the walls of the microwells are inclined slightly outwards, the diameter at the open end being in the range of about 0.100 to 0.108 inches, and the depth of microwells is in the range of about 0.100 to 0.108 inches.

11. The rotor of claim 4 wherein the microchannels have a width in the range of 0.014 to 0.016 inches and a depth in the range of about 0.014 to 0.016 inches.

12. The rotor of claim 9 wherein the layer of tape stock is about 2 to 4 mils thickness and is made of a plastic material like polypropylene or polyester.

13. The rotor of claim 1 comprising a body of polystyrene material.

14. The rotor of claim 1 wherein the source of rotational energy is a motor operable during an initial filling with liquid in the range of about 200 to 400 RPM and also during a subsequent distribution of liquid in the range of about 4,000 to 6,000 RPM.

* * * * *